United States Patent
Montes De Oca Balderas et al.

(10) Patent No.: US 11,666,729 B2
(45) Date of Patent: Jun. 6, 2023

(54) METHODS OF BONDING COMPONENTS TO POLYMERIC SUBSTRATES

(71) Applicant: Hollister Incorporated, Libertyville, IL (US)

(72) Inventors: Horacio Montes De Oca Balderas, Ballina (IE); Eamonn Casey, Ballina (IE); Claire McKenna, Castlebar (IE); John P. O'Mahony, Ardnacrusha (IE)

(73) Assignee: Hollister Incorporated, Libertyville, IL (US)

( * ) Notice: Subject to any disclaimer, the term of this patent is extended or adjusted under 35 U.S.C. 154(b) by 243 days.

(21) Appl. No.: 16/760,641

(22) PCT Filed: Nov. 1, 2018

(86) PCT No.: PCT/US2018/058623
§ 371 (c)(1),
(2) Date: Apr. 30, 2020

(87) PCT Pub. No.: WO2019/089875
PCT Pub. Date: May 9, 2019

(65) Prior Publication Data
US 2020/0345973 A1    Nov. 5, 2020

Related U.S. Application Data

(60) Provisional application No. 62/581,427, filed on Nov. 3, 2017.

(51) Int. Cl.
| | |
|---|---|
| A61M 25/00 | (2006.01) |
| B29C 65/48 | (2006.01) |
| B29C 65/00 | (2006.01) |
| C08J 5/12 | (2006.01) |
| C08J 7/056 | (2020.01) |
| C08J 7/02 | (2006.01) |

(52) U.S. Cl.
CPC ..... A61M 25/0014 (2013.01); B29C 65/4895 (2013.01); B29C 66/52 (2013.01); B29C 66/534 (2013.01); B29C 66/71 (2013.01); C08J 5/122 (2013.01); C08J 7/02 (2013.01); C08J 7/056 (2020.01); C08J 2353/00 (2013.01); C08J 2493/00 (2013.01)

(58) Field of Classification Search
CPC .......... C08J 7/02; C08J 5/122; C08J 2353/00; C08J 2493/00; B29C 65/4895; B29C 66/52; B29C 66/534; B29C 66/71; B32B 27/24; B32B 2038/0088; A61M 25/0014; A61M 25/1025; B29L 2031/7542
USPC ..................................................... 156/308.6
See application file for complete search history.

(56) References Cited

U.S. PATENT DOCUMENTS

| | | | |
|---|---|---|---|
| 3,726,741 A | 4/1973 | Middlebrook | |
| 3,923,722 A | 12/1975 | Lakshmanan | |
| 3,970,623 A * | 7/1976 | Feeney | C08F 236/06 |
| | | | 526/86 |
| 3,981,851 A | 9/1976 | Plueddemann | |
| 4,695,276 A | 9/1987 | Shinno | |
| 4,776,849 A | 10/1988 | Shinno | |
| 4,781,703 A | 11/1988 | Walker | |
| 5,203,943 A | 4/1993 | Nornberg | |
| 5,330,449 A | 7/1994 | Prichard | |
| 5,922,443 A * | 7/1999 | Larsen | C08J 3/18 |
| | | | 428/423.1 |
| 6,074,379 A | 6/2000 | Prichard | |
| 6,310,140 B1 * | 10/2001 | Raetzsch | C08L 53/00 |
| | | | 525/193 |
| 7,455,325 B2 | 11/2008 | Mejlhede | |
| 8,168,249 B2 | 5/2012 | Utas | |
| 8,735,491 B2 | 5/2014 | Kim | |
| 8,998,882 B2 | 4/2015 | Knapp | |
| 9,062,803 B2 | 6/2015 | Bourgeois | |
| 9,192,740 B2 | 11/2015 | Frojd | |
| 9,339,640 B2 | 5/2016 | Nikitina | |
| 9,408,946 B2 | 8/2016 | Utas | |
| 9,694,113 B2 | 7/2017 | Knapp | |
| 9,937,334 B2 | 4/2018 | Frojd | |
| 10,518,000 B2 | 12/2019 | Knapp | |
| 2002/0002363 A1 | 1/2002 | Urakawa | |
| 2004/0162460 A1 | 8/2004 | Shah | |
| 2007/0015871 A1 | 1/2007 | Nakamura | |
| 2010/0239802 A1 | 9/2010 | Kuwahara | |
| 2011/0058982 A1 * | 3/2011 | Kaneko | A61L 2/087 |
| | | | 422/22 |
| 2011/0251596 A1 | 10/2011 | Kim | |
| 2011/0319837 A1 * | 12/2011 | Uehara | B32B 27/34 |
| | | | 138/177 |
| 2012/0048380 A1 | 3/2012 | Thomas | |
| 2012/0150150 A1 * | 6/2012 | Cai | F16L 33/34 |
| | | | 604/524 |
| 2012/0172848 A1 | 7/2012 | Gustavsson | |
| 2013/0123678 A1 | 5/2013 | Carty | |
| 2013/0316107 A1 | 11/2013 | Oleson | |
| 2014/0150782 A1 | 6/2014 | Vazales | |
| 2014/0288517 A1 | 9/2014 | Tsai | |
| 2015/0112314 A1 | 4/2015 | Gustavsson | |

(Continued)

FOREIGN PATENT DOCUMENTS

| | | | |
|---|---|---|---|
| CN | 102101997 A * | 6/2011 | |
| CN | 106189041 A | 12/2016 | |

(Continued)

OTHER PUBLICATIONS

Machine translation of CN 102101997 date uknown.*
International Preliminary Report on Patentability dated May 5, 2020 for International Application No. PCT/US2018/058623.

Primary Examiner — John L Goff, II
(74) Attorney, Agent, or Firm — Cook Alex Ltd.

(57) ABSTRACT

Methods for bonding polymeric substrates to component parts, and medical devices assemblies including a tubing and a component part bonded together using a solvent containing a tackifier.

21 Claims, No Drawings

(56) References Cited

U.S. PATENT DOCUMENTS

| | | |
|---|---|---|
| 2015/0368419 A1 | 12/2015 | Randall |
| 2016/0030728 A1 | 2/2016 | Bourgeois |
| 2017/0296704 A1 | 10/2017 | Knapp |
| 2019/0262579 A1 | 8/2019 | Lovmar |
| 2020/0086620 A1 | 3/2020 | Sevinc |

FOREIGN PATENT DOCUMENTS

| | | | |
|---|---|---|---|
| EP | 1149598 A2 | 10/2001 | |
| EP | 0907384 B1 | 2/2003 | |
| EP | 1599249 B1 | 11/2006 | |
| EP | 2407512 A1 | 1/2012 | |
| EP | 1745807 B1 | 8/2012 | |
| EP | 2279767 B1 | 8/2012 | |
| EP | 2358806 B1 | 10/2015 | |
| EP | 2674185 B1 | 11/2016 | |
| EP | 2292294 B1 | 8/2017 | |
| EP | 3178514 A1 | 10/2017 | |
| EP | 2976215 B1 | 8/2019 | |
| EP | 3191290 B1 | 5/2020 | |
| JP | 01149876 A | 12/1989 | |
| JP | 2008201994 A | 9/2008 | |
| NL | 7217489 A | 12/1974 | |
| WO | 9749437 A1 | 12/1997 | |
| WO | 2004071568 A1 | 8/2004 | |
| WO | 2007011287 A1 | 1/2007 | |
| WO | 2010074896 A2 | 7/2010 | |
| WO | 2011026929 A1 | 3/2011 | |
| WO | 2012089737 A1 | 7/2012 | |
| WO | 2012109626 A2 | 8/2012 | |
| WO | 2014153334 A1 | 9/2014 | |
| WO | 2014165046 A1 | 10/2014 | |
| WO | 2016018577 A1 | 2/2016 | |
| WO | WO-2016020774 A1 * | 2/2016 | ............... A61F 6/04 |
| WO | 2016100848 A1 | 6/2016 | |
| WO | 2017097956 A1 | 6/2017 | |
| WO | 2020061201 A2 | 3/2020 | |

* cited by examiner

METHODS OF BONDING COMPONENTS TO POLYMERIC SUBSTRATES

RELATED APPLICATION

The present application is the U.S. National Stage Application of PCT Application No. PCT/US2018/058623, filed Nov. 1, 2018, which claims the benefit of and priority to U.S. Provisional Patent Application No. 62/581,427, filed Nov. 3, 2017, both of which are hereby incorporated herein by reference.

TECHNICAL FIELD

The present disclosure generally relates to methods of bonding a component part to a polymeric substrate, such as a medical tube, and medical device assemblies made from such methods.

BACKGROUND

Several medical devices include a component part attached to a substrate. For example, medical tubes commonly include a component part attached thereto. Such component parts may include drainage members, connectors, joints, etc. In the field of urinary catheters, for instance, the catheter tube (polymeric substrate) has a drainage member (component part) connected to the catheter tube.

In many instances, component parts are attached to the substrates by over-molding or adhesives, such as UV curable adhesives. While the use of over-molding or adhesives may provide adequate bonding or attachment, attachment by these mechanisms can oftentimes add time and expense to the manufacturing process. For example, when a UV curable adhesive is used, the adhesive is exposed to a UV energy source for a period of time. This requires the addition of a UV light curing system or box to the manufacturing line and additional time is added to the manufacturing process to provide for the UV curing. Similarly, when over-molding is employed, an injection molding tool is typically required on the manufacturing line and additional time is required for cooling of the over mold prior to further processing of the medical device.

Solvent bonding is a common and inexpensive method used to bond compatible materials such as PVC, polystyrene and polyurethanes. Solvents, such as cyclohexanone, are commonly used for solvent bonding. However, certain materials are not suitable for solvent bonding or do not form strong bonds. Such materials include, but are not limited to, thermoplastic olefins and thermoplastic elastomer block copolymers based on SEBS, SBS and SIS and blends of block copolymer elastomer with polyolefins, PEBAX, EVA and other polymeric modifiers.

Therefore, there still remains a need for methods of bonding medical substrates to component parts.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of bonding a component part to a polymeric substrate, comprises applying a solvent containing a tackifier to a surface of at least one of a polymeric substrate and a component part wherein the one of the polymeric substrate and the component part to which the solvent is applied is made from a block copolymer that is compatible with the tackifier. The polymeric substrate is contacted to the component part to form a bond therebetween.

In another aspect, a medical tube set comprising a medical tube and a component part, wherein at least one of the medical tube and the component part is made from a block copolymer and wherein the component part and the tubing are bonded together using a solvent containing tackifier.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present application discloses methods of bonding a component part to a polymeric substrate. The methods may include applying a solvent containing a tackifier to a surface of at least one of the polymeric substrate and the component part. The solvent swells or partially swells the materials to which it is applied, allowing some of the tackifier to penetrate into the material. The one of the polymeric substrate and the component part to which the solvent is applied may be made from a block copolymer that is compatible with the tackifier such that the surface of the one of the polymeric substrate and component part becomes pressure sensitive or pressure sensitive-like after application of the solvent. In one embodiment, the material becomes pressure sensitive/pressure sensitive-like after application and drying of the solvent. The polymer substrate and the component part are placed in contact with each other, thereby bonding the component part to the polymer substrate.

In one embodiment, the polymeric substrate and/or the component part may be made from a thermoplastic elastomer (TPE) in that the substrate and/or component part may be made solely or mostly of a TPE or the substrate and component part may include a TPE. For example, the substrate and/or component part may be formed from TPE compounded with other polymers. In one embodiment, the TPE may be compounded with, for example, a polyolefin such as polypropylene, polyethylene, polyamide block copolymer, polyurethane, polyester, EVA and the like.

The TPE may be a block copolymer, such as a styrenic block copolymer TPE. Such stryenic block copolymer TPEs may include styrene-butadiene-styrene (SBS) or styrene-ethylene-butylene-styrene (SEBS). Such SEBS and SBS TPE materials are commonly, but not exclusively, sold under the tradename Kraton®. In one embodiment, the SEBS may have a styrene content of greater than 20%. The styrene content may be higher or lower depending on the desired application. Furthermore, the substrate and/or component part may be made from SBS or SEBS compounded with another polymer, such as a polyolefin (which may be for example, polypropylene, polyethylene, polyamide block copolymer, polyurethane, polyester, and the like).

The solvent applied to the substrate and/or component part includes a tackifying resin/tackifier. Regarding the solvent, it may be sufficiently strong to swell or partially swell the TPE material of the substrate and/or component part. While the solvent may also dissolve or partially dissolve the TPE material, dissolving the TPE is not required. The solvents may include, for example, cyclohexanone, toluene, methyl ethyl ketone, tetrahydrofuran, xylene, isopropanol alcohol, heptane or mixtures thereof. In one embodiment, the solvent may be a blend that includes cyclohexanone and methyl ethyl ketone. In another embodiment, the blend may be toluene and methyl ethyl ketone. In each of these blends, the cyclohexanone or toluene may be at about a 2:1 ratio to the methyl ethyl ketone. For example, the blend may include a 70:30 ratio of cyclohexanone to methyl ethyl ketone or a 70:30 ratio of toluene to methyl ethyl ketone.

Turning to the tackifier, preferably, the tackifier is compatible with the mid-block of the block copolymer of the TPE. For example, when the TPE is SBS or SEBS, the tackifier may be compatible with the mid-block of these copolymers. In one embodiment, the tackifier may be hydrogenated wood rosin (such a Foral 105E supplied by Eastman), a terpene phenolic such as Sylvarez TP105 (Arizona Chemical) or a C5 or C9 hydrocarbon based resin or combinations thereof.

Furthermore, the solvent may also include other additives, such as an amount of SEBS or SBS.

In one embodiment, the solvent containing a tackifier may include between about 92 wt % and about 98 wt % solvent and between about 2 wt % and about 8 wt % tackifier. In one embodiment, the tackifier may be less than about 20 wt % or 8 wt % or 6 wt % of the solvent containing a tackifier. For example, the solvent containing a tackifier may include about 95 wt % of the solvent and about 5 wt % tackifier. The solvent may be, for example, a blend of cyclohexanone/methyl ethyl ketone at a weight ratio of 70:30 and the tackifier may be hydrogenated wood rosin. In another example, the solvent containing a tackifier may include about 92 wt % solvent, about 4 wt % tackifier and about 4 wt % of an additive. The solvent may be, for example, a blend of toluene/methyl ethyl ketone at a weight ratio of 70:30, the tackifier may be hydrogenated wood resin and the additive may be SEBS or SBS.

In one embodiment of a method of attaching a drainage member to a catheter tube, the drainage member and/or the catheter tube may be made of a TPE, such as any of the TPEs described above. A solvent containing a tackifier, such as any of those described above, is applied to the outer surface of the catheter and/or the inner surface of the drainage member. The solvent containing a tackifier may be applied by dip coating, spraying, brushing or any other suitable application process. The catheter tube is then contacted with the drainage member, such that the surface(s) to which the solvent containing a tackifier was applied is placed in contact with another surface to bond the surfaces. For example, the catheter tube may be inserted into an end of the drainage member so that the surface of the outer surface of the catheter tube contacts the inner surface of the drainage member. The surface of the catheter tube bonds to that of the drainage member, thereby bonding the drainage member to the catheter tube. Because this bonding occurs relatively quickly, the catheter tube can proceed with further processing in the manufacturing process. In one embodiment, the bond may form in about 60 seconds or less. Thus, the catheter tubes having the drainage member bonded thereto may relatively quickly proceed to application of a coating, such as a hydrophilic coating, packaging and radiation sterilization. The radiation sterilization may be, for example, gamma or E-beam radiation at a dose between about 25 kGy and 45 kGy. Furthermore, when the catheter includes a hydrophilic coating, the catheter may be packaged in contact with a wetting fluid.

Thus, the methods may be employed to produce a medical tube set comprising a medical tube and a component part, wherein at least one of the medical tube and the component part is made from a block copolymer and wherein the component part and the tubing are bonded together using a solvent containing a tackifier.

Catheter and drainage members bonded by the above methods may have bond strengths of greater than about 40 N. For example, the bond strengths may be above 70 N or above 80 N. Surprisingly, it was found that the bond strengths improved after the bonded materials have been exposed to radiation. For example, the bond strength may improve after receiving a dose between about 25 kGy and 45 kGy of gamma or E-beam radiation. In one embodiment, the bond increases following sterilization by E-beam or gamma radiation. The bond strengths may be measured by using a tensile tester with the drainage member and tubing clamped 5 cm apart and pulled at 10 mm/sec until failure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method of solvent bonding a drainage member to a urinary catheter tube, the method comprising:
    applying a solvent containing a tackifier to a surface of at least one of the urinary catheter tube and the drainage member, wherein the urinary catheter tube and the drainage member are made from thermoplastic elastomer material;
    wherein the solvent swells the thermoplastic elastomer material;
    allowing the tackifier to penetrate the thermoplastic elastomer material;
    contacting the urinary catheter tube to the drainage member to form a bond therebetween; and
    exposing the bonded urinary catheter tube and drainage member to a selected dose of radiation.

2. The method of claim 1 wherein the thermoplastic elastomer material comprises a styrenic block copolymer.

3. The method of claim 1 wherein the thermoplastic elastomer material comprises styrene ethylene butylene styrene polymer or styrene butylene styrene.

4. The method of claim 3 wherein the styrene content is greater than 20 weight percent.

5. The method of claim 1 wherein the urinary catheter tube and the drainage member are made from a blend of thermoplastic elastomer and a second polymer.

6. The method of claim 5 wherein the second polymer comprises a polyolefin.

7. The method of claim 1 wherein the solvent comprises one or more of cyclohexanone, toluene, methyl ethyl ketone, xylene, isopropanol and tetrahydrofuran.

8. The method of claim 1 wherein the tackifier is compatible with the thermoplastic elastomer material.

9. The method of claim 1 wherein the tackifier comprises a hydrogenated rosin.

10. The method of claim 9 wherein the tackifier comprises an ester of hydrogenated rosin.

11. The method of claim 1 wherein the tackifier is in the amount of less than 20 wt % of the solvent containing the tackifier.

12. The method of claim 1 wherein the solvent containing the tackifier is applied to the surface of the catheter tube.

13. The method of claim 1 wherein the solvent containing the tackifier is applied to the surface of the drainage member.

14. The method of claim 1 wherein the solvent containing the tackifier further includes styrene-ethylene-butadiene-styrene or styrene-butadiene-styrene.

15. The method of claim 1, wherein the radiation is gamma radiation.

16. The method of claim 1, wherein the radiation is ebeam radiation.

17. The method of claim 1, wherein the selected dose of radiation is from about 25 kGy-45 kGy.

18. The method of claim 1, wherein the bond strength between the catheter tube and the drainage member is at least 40 N.

19. The method of claim 1, wherein the bond strength between the catheter tube and the drainage member is at least 70 N.

20. The method of claim 1, wherein the solvent content is from about 92%-98% and the tackifier content is from about 2% to about 8% in the solvent containing a tackifier.

21. The method of claim 1, wherein the solvent containing a tackifier is a solvent blend consisting of solvent and tackifier.

\* \* \* \* \*